United States Patent
Williams et al.

(10) Patent No.: US 6,623,730 B1
(45) Date of Patent: Sep. 23, 2003

(54) THERAPEUTIC USES OF POLYMERS AND OLIGOMERS COMPRISING GAMMA-HYDROXYBUTYRATE

(75) Inventors: Simon F. Williams, Sherborn, MA (US); David P. Martin, Arlington, MA (US)

(73) Assignees: Tepha, Inc., Cambridge, MA (US); Metabolix, Inc., Cambridge, MA (US)

( * ) Notice: Subject to any disclaimer, the term of this patent is extended or adjusted under 35 U.S.C. 154(b) by 99 days.

(21) Appl. No.: 09/661,948

(22) Filed: Sep. 14, 2000

Related U.S. Application Data

(60) Provisional application No. 60/182,371, filed on Feb. 14, 2000, and provisional application No. 60/153,844, filed on Sep. 14, 1999.

(51) Int. Cl.$^7$ ......... A61K 31/765; A61K 9/20; A61K 9/70; A61K 13/00; C07C 69/66

(52) U.S. Cl. ............ 424/78.37; 424/464; 424/449; 424/422; 560/185

(58) Field of Search ............ 424/78.37, 464, 424/451, 449, 422; 514/533, 923, 962, 2, 557; 560/185

(56) References Cited

U.S. PATENT DOCUMENTS

| | | | |
|---|---|---|---|
| 5,563,239 A | 10/1996 | Hubbs et al. | |
| 5,753,708 A | 5/1998 | Koehler et al. | |
| 5,840,331 A | * 11/1998 | Van Cauter et al. | ........ 424/464 |
| 5,990,162 A | * 11/1999 | Scharf | ........ 514/533 |

FOREIGN PATENT DOCUMENTS

| | | |
|---|---|---|
| EP | 0 429 403 A2 | 5/1991 |
| EP | 0 344 704 A1 | 12/1991 |
| WO | WO 97/15681 A1 | 5/1997 |
| WO | WO 97/30042 A1 | 8/1997 |
| WO | WO 99/14313 A2 | 3/1999 |
| WO | WO 99/32536 A1 | 7/1999 |
| WO | WO 99/35192 A1 | 7/1999 |
| WO | WO 99/35192 * | 7/1999 |

OTHER PUBLICATIONS

Abate, et al., "Separation and structural characterizations of cyclic and open chain oligomers produced in the partial pyrolysis of microbial poly(hydroxyutyrates)," *Macromolecules* 28(23):7911–1916 (1995).

Addolorato, et al., "Maintaining abstinence from alcohol with gamma–hydroxybutyric acid," *The Lancet* 351:38 (1998).

Agostini, et al., "Synthesis and Characterization of Poly–β–Hydroxybutyrate. I. Synthesis of Crystalline DL Poly–β–Hydroxybutyrate from DL– β–Butyrolactone," *Polym. Sci.* Part A–1, 9:2775–2787 (1971).

Andriamampandry, et al., "Cloning of a rat brain succinic semialdehyde reductase involved in the synthesis of the neuromodulator γ–hydroxybutyrate," *Biochem. J.* 334:43–50 (1998).

Byrom, "Miscellaneous Biomaterials," in *Biomaterials* (D. Byrom, ed.) pp. 333–359 (MacMillan Publishers, London 1991).

Colombo, et al., "Involvement of GABA(A) and GABA(B) receptors in the mediation of discriminative stimulus effects of gamma–hydroxybutyric acid," *Physiology & Behavior* 64:293–302 (1998).

Dubois, et al., "Macromolecular Engineering of Polylactones and Polylactides. 12. Study of the Depolymerization Reactions of Poly (ε–caprolactone) with Functional Aluminum Alkoxide End Groups," *Macromolecules* 26:4407–12 (1993).

Entholzner, et al., "EEG changes during sedation with gamma–hydroxybutyric acid," *Anaesthesist* 44:345–350 (1995).

Gerra, et al., "Flumazenil effects on growth hormone response to gamma–hydroxybutyric acid," *International Clinical Psychopharmacology* 9:211–215 (1994).

Gross, et al., "Polymerization if β–monosubstituted–b–propiolactones using trialkylaminimum–water catalytic systems and polymer characterization," *Macromolecules* 21:2657–2668 (1988).

Hocking & Marchessault, "Syndiotactic poly[(R, S)–β–hydroxybutyrate] isolated from methylaluminoxane–catalyzed polymerization," *Polym. Bull.* 30:163–170 (1993).

Hocking & Marchessault, "Biopolyesters" Griffin, Ed., "Chemistry and Technology of Biodegradable Polymers," pp. 48–96 (Chapman and Hall, London, 1994).

Holmes, "Biologically Produced (R)–3–hydroxyalkanoate Polymers and Copolymers," in Bassett Ed., "Developments in Crystalline Polymers," pp. 1–65 (Elsevier, London, vol. 2, 1988).

Hori, et al., "Ring–Opening Copolymerization of Optically Active β–Butyrolactone with Several Lactones Catalyzed by Distannoxane Complexes: Synthesis of New Biodegradable Polyesters," *Macromolecules* 26:4388–4390 (1993).

(List continued on next page.)

*Primary Examiner*—Thurman K. Page
*Assistant Examiner*—Blessing Fubara
(74) *Attorney, Agent, or Firm*—Holland & Knight LLP

(57) ABSTRACT

Oligomers and polymer compositions are provided which comprise GHB and produce GHB after administration in vivo. Devices for the storage and delivery of these polymers and oligomers are also provided. These oligomers and polymer compositions are useful in a variety of applications. The compositions can be used therapeutically, for example, in the treatment of patients with narcolepsy, chronic schizophrenia, catatonic schizophrenia, atypical psychoses, chronic brain syndrome, neurosis, alcoholism, drug addiction and withdrawal, Parkinson's disease and other neuropharmacological illnesses, hypertension, ischemia, circulatory collapse, radiation exposure, cancer, and myocardial infarction. Other uses for the compositions include anesthesia induction, sedation, growth hormone production, heightened sexual desire, anorectic effects, euphoria, smooth muscle relaxation, muscle mass production, and sleep, including rapid eye movement sleep. In a still further embodiment, the oligomers and polymers may be used to produce absence seizures.

29 Claims, No Drawings

OTHER PUBLICATIONS

Hori, et al., "Ring–Opening Polymerization of Optically Active β–Butyrolactone Using Distannoxane Catalysts: Synthesis of High Molecular Wright Poly(3–hydroxybutyrate)," *Macromolecules* 26:5533–5534 (1993).

Horowitz, et al., *Macromolecules* 32:3347–3352 (1999).

Kaufman & Nelson, "An overview of gamma–hydroxybutyrate catabolism: the role of the cytosolic NADP(+)–dependent oxidoreductase EC 1.1.1.19 and of a mitochondrial hydroxyacid–oxoacid transhydrogenase in the initial, rate–limiting step in this pathway," *Neurochemical Research* 16:965–974 (1991).

Kemnitzer, et al., "Preparation of predominantly Syndiotactic Poly(β–hydroxybutyrate) by the Tributylin Methoxide Catalyzed Ring–Opening Polymerization of racemic β–Butyrolactone," *Macromolecules* 26:1221–1229 (1993).

Kleinschmidt, et al., "Continuous sedation during spinal anaesthesia: gamma–hydroxybutyrate vs. propofol," *European Journal of Anaesthesiology* 16:23–30 (1999).

Kleinschmidt, et al., "Total intravenous anaesthesia using propofol, gamma–hydroxybutyrate or midazolam in combination with sufentanil for patients undergoing coronary artery bypass surgery," *European Journal of Anesthesiology* 14:590–599 (1997).

Lafferty et al.,"Microbial Production of Poly–β–hydroxybutyric acid," Rehm and Reed, Eds., "Biotechnology" Verlagsgesellschaft, Weinheim, vol. 66, 1988, pp. 135–176.

Le Borgne & Spassky, "Stereoelective polymerization of β–butyrolactone," *Polymer* 30:2312–2319 (1989).

Lebedev & Yevstropov, *Makromol. Chem.* 185:1235–1253 (1984).

Madison & Huisman, "Metabolic engineering of poly(3–hydroxyalkanoates): from DNA to plastic," *Microbiol. Mol. Biol. Rev.* 63–:21–53 (1999).

Müller & Seebach, "Poly(hydroxyalkanoates): A Fifth Class of Physiologically Important Organic Biopolymers," *Angew. Chem. Int. Ed. Engl.* 32:477–502 (1993).

Nelson, et al., "The extraneural distribution of gamma–hydroxybutyrate," *J. Neurochem.* 37:1345–1348 (1981).

Reynolds, *Martindale: The Extra Pharmacopeia*, p. 1264, (Thirty First Edition, Royal Pharmaceutical Society, London, 1997).

Ropero–Miller & Goldberger, "Recreational drugs. Current trends in the 90s," *Clinics in Laboratory Medicine*, 18:727–746 (1998).

Saito, et al., "Microbial Synthesis and properties of Poly(3–hydroxybutyrate–co–4–hydroxybutyrate)," *Polymer International* 39:169–174 (1996).

Scharf, et al., "Pharmacokinetics of gammahydroxybutyrate (GHB) in narcoleptic patients," *Sleep* 21:507–514 (1998).

Sendelbeck & Girdis, "Disposition of a 14C–labeled bioerodible polyorthoester and its hydrolysis products, 4–hydroxybutyrate and cis,trans–1,4–bis(hydroxymethyl) cyclohexane, in rats," *Drug Metabolism & Disposition* 13:291–295 (1985).

Snead, "The gamma–hydroxybutyrate model of absence seizures: correlation of regional brain levels of gamma–hydroxybutyric acid and gamma–butyrolactone with spike wave discharges," *Neuropharmacology* 30:161–167 (1991).

Song, et al., *Biotechnol. Lett.* 21:193–197 (1999).

Steinbüchel, "Polyhydroxyalkanoic Acids," in Byrom Ed., "Biomaterials" MacMillan Publishers, London, 1991, pp. 123–213.

Tanahashi & Doi, "Thermal Properties and Stereoregularity of Poly(3–hydroxybutyrate) Prepared from optically Active β–Butyrolactone with a Zinc–Based Catalyst," *Macromolecules* 24:5732–5733 (1991).

Tanaka, et al., "Clinical application of 4–hydroxybutyrate sodium and 4–butyrolactone in neuropsychiatric patients," *Folia Psychiatrica et Neurologica* 20:9–17 (1966).

Tunnicliff, "Sites of action of gamma–hydroxybutyrate (GHB)—a neuroactive drug with abuse potential," *Clincial Toxicology* 35:581–590 (1997).

Williams & Peoples, "Biodegradable plastics from plants," *CHEMTECH* 26:38–44 (1996).

Williams & Peoples, "Making Plastics Green," *Chem. Br.* 33:29–32 (1997).

Williams, et al., "PHA applications: addressing the price performance issue I. Tissue engineering," *Int. J. Biol. Macromol.* 25:111–121 (1999).

Xie, et al., "Ring–opening Polymerization of β –butyrolactone by Thermophilic Lipases," *Macromolecules* 30:6997–6998 (1997).

* cited by examiner

THERAPEUTIC USES OF POLYMERS AND OLIGOMERS COMPRISING GAMMA-HYDROXYBUTYRATE

CROSS-REFERENCE TO RELATED APPLICATION

Priority is claimed to U.S. provisional applications Ser. No. 60/153,844, filed Sep. 14, 1999, and Ser. No. 60/182,371, filed Feb. 14, 2000.

BACKGROUND TO THE INVENTION

The present invention is generally in the field of therapeutic formulations for delivering gamma-hydroxybutyrate.

Gamma-hydroxybutyrate ("GHB") is a naturally occurring substance that is widely distributed in the mammalian body, being present, for example, in the brain, kidney, heart, liver, lung and muscle (Nelson, et al., *J. Neurochem.*, 37:1345–48 (1981)). When administered exogenously, GHB readily crosses the blood-brain barrier and penetrates the brain, producing a number of neuropharmacological effects. For over 35 years, GHB has been used as an intravenous agent for the induction of anesthesia and for long-term sedation, without serious side-effects on circulation or respiration (Entholzner, et al., *Anesthetist*, 44:345–50 (1995)), and without an accompanying seizure-inducing activity in humans (Tunnicliff, *Clinical Toxicology*, 35:581–90 (1997)). Patients with chronic schizophrenia characterized by autism, inactivity, and apathy; catatonic schizophrenia; chronic schizophrenia with hallucination and delusion; atypical psychoses; and chronic brain syndrome due to trauma, as well as neurotic patients (Tanaka, et al., *Folia Psychiatrica et Neurologica*, 20:9–17 (1966)), have all been treated using GHB. It also has recently been suggested that GHB may be a suitable agent for total intravenous anesthesia in patients with coronary artery disease (Kleinschmidt, et al., *Euro. J. Anesthesiology*, 14:590–99 (1997)), as well as for sedation during spinal anesthesia (Kleinschmidt, et al., *Euro. J. Anaesthesiology*, 16:23–30 (1999)).

In addition to these uses, GHB also is used to treat narcolepsy, a chronic sleep disorder that usually begins in adolescence or early adulthood and lasts hroughout life. Narcolepsy is characterized by sudden sleep attacks lasting usually from a few to thirty minutes, paralysis upon lying down or waking, visual or auditory hallucinations at the onset of sleep, and temporary loss of muscle tone while awake (cataplexy) or asleep. Treatment with GHB substantially reduces these signs and symptoms of narcolepsy in humans (Scharf, *Sleep*, 21:507–14 (1998)).

Other uses of GHB include its application in the pharmacotherapy of alcoholism, where it has been found to reduce alcohol craving and consumption, and to ameliorate symptoms of alcohol withdrawal syndrome in alcoholics (Colombo, et al., *Physiology & Behavior*, 64:293–302 (1998); Addolorato, et al., *The Lancet*, 351:38–(1998) and references therein). GHB also reportedly aids patients undergoing withdrawal from opiates (Andriamampandry, et al., *Biochem. J.* 334:43–50 (1998) and references therein) and relieves anxiety, tremor, and muscle rigidity in patients with Parkinson's disease (Tanaka, et al., *Folia Psychiatrica et Neurologica*, 20:9–17 (1966)). Administration of GHB also has been reported to protect neurons and intestinal epithelium against cell death resulting from experimental ischemia (Kaufman & Nelson, *Neurochemical Research*, 16:965–74 (1991) and references therein), to drop blood pressure in hypertensive patients (Tanaka, et al., *Folia Psychiatrica et Neurologica*, 20:9–17 (1966)), to increase plasma levels of growth hormone after injection in healthy subjects (Gerra, et al., *Int'l Clinical Psychopharmacology*, 9:211–15 (1994)), and to stimulate growth hormone and prolactin production (U.S. Pat. No. 5,840,331 to Van Cauter, et al.). Administration of GHB also is purported to be an effective anorectic, heighten sexual desire, produce pleasurable effects such as euphoria and smooth muscle relaxation, promote muscle mass, and be able to induce rapid eye movement sleep (Ropero-Miller & Goldberger, *Clinics in Laboratory Medicine*, 18:727–46 (1998)). PCT WO 99/09972 and U.S. Pat. No. 5,990,162 to Scharf discloses the use of GHB in treatment of fibromyalgia and chronic fatigue syndrome. Administration of GHB also has been shown to increase gastric emptying (Poggioli, et al., *Life Sci.* 64:2149–54 (1999)), and could be used as a prokinetic drug for treatment of a number of conditions where improvement in gastrointestinal motility and gastric emptying is desired. Such conditions include treatment of malabsorption disorders, and increased uptake of poorly absorbed drugs. Gamma-butyrolactone which is metabolized to GHB has been shown to potentiate the effect of gamma-aminobutyric acid on gastric secretions (Watanabe, et al., *Jpn. J. Pharmacol.* 33:1163–69 (1983)). GHB has shown anti-ulcer activity against ulcers induced by indomethacin, restraint stress or pyloric ligation (Yong, et al., *Chung Kuo Yao Li Hsueh Po*; 10:350–53 (1989)). Other uses of GHB have been described in Tanaka, et al., *Folia Psychiatrica et Neurologica*, 20:9–17 (1966).

In animals, GHB produces electroencephalographic (EEG) and behavioral changes, resembling generalized absence seizures. The treated animals show arrest of activity which can be aborted by anti-absence drugs. For this reason, GHB has been used to provide a reproducible, consistent, pharmacologically specific model for the study of generalized absence seizures, which is analogous to other models of absence in the rat (Snead, *Neuropharmacology*, 30:161–67 (1991) and references therein). GHB administration also has been used in animals to normalize cardiovascular function of hemorrhage and as an anti-ischemic (Cash, *Neuroscience & Behavioral Rev.*, 18:291–304, 1994). In mice, GHB was found to exert a radioprotective effect (Cash, *Neuroscience & Behavioral Rev.*, 18:291–304 (1994)).

Infusion of GHB also has been found to possess an angiogenesis inhibitory effect, making GHB potentially useful in the treatment of cancer as an anti-angiogenesis agent (Yonekura, et al., *Clin. Cancer Res.*, 5:2185–91 (1999)). GHB also has been used prophylactically in rats as an antihypoxant, antioxidant, or actoprotector, increasing survival rates of rats with myocardial infarction (Dubovaia, et al., *Eksp. Klin. Farmakol.* 59:51–54 (1996); Tsorin, et al., *Eksp. lin. Farmakol.* 56:25–27 (1993)). GHB reportedly prevents heart damage after acute blood loss (Meerson, et al., *Kardiologiia* 22:38–44 (1982)).

GHB may also be administered prophylactically to reduce inflammation or ischemic or reperfusion injury during surgery. Prophylactic administration of GHB prevented liver damage to tetrachloromethane poisoning (*Eksp Kim Farmakol.*, 59(4):51–54 (1996)). The lithium salt of GHB depressed carrageenan inflammation in a hamster cheek pouch assay (Aleksandrov & Speranskaia, *Biull. Eskp. Biol. Med.* 106:233–35 (1988)) Prophylactic administration of lithium salt of GHB prevented inflammation in acute paw edema assay (Aleksandrov & Speranskaia, *Biull. Eskp. Biol. Med.* 103:188–90 (1987)). GHB has been shown to improve blood flow to ischemic heart tissue (Matsievskii, et al., *Biull Eksp Biol. Med*; 106:531–33 (1988)). GHB also has been used to protect frozen liver tissue for transplantation (Sherman, et al., *Transplantation* 57:8–11 (1994)).

Sodium 4-hydroxybutyrate has been shown to affect metabolism (Petrin, et al., *Vopr. Med Khim*, 39:36–39 (1993)), as its administration reduced nucleotide catabolism, glycolysis, lipolysis, and lipid peroxidation. Sodium hydroxybutyrate also has been shown to stimulate the pentosophosphate cycle and interfere with metabolic acidosis (Lopatin, et al., *Farmakol. Toksikol*, 47:53–55 (1984). Thus GHB may be used to improve me damaging effects of injury, surgery, ischemia and shock.

GHB has been shown to prevent the proliferation of cancer and functions as an antineoplastic agent (Basaki, et al., *Gan To Kagaku Ryoho*, 27:93–98 2000)). GHB and gamma-butyrolactone have been shown to reduce angiogenesis induced by certain types of cancer cells (Yonekura, et al., Clinical *Cancer Research*, 5:2185–91 (1999)). GHB also has been shown to be beneficial for the treatment of lung cancer patients during and after surgery (Leonenkov, et al., *Vopr. Onkol*, 39:75–79 (1993)) and this benefit was attributed to the antihypoxic effects of GHB. Accordingly, GHB can be used to prevent the spread or proliferation of a cancer.

While significant progress has clearly been made in the development of therapeutic and experimental uses for GHB, there have been a number of problems associated with the development of these uses which have hindered or prevented further progress, or made treatment difficult or more burdensome to manage. These problems include the development of hypernatremia and metabolic alkalosis as a result of delivering large doses of GHB, which is administered as a sodium salt rather than a free acid, especially over prolonged periods (Entholzner, E. et al., *Anaesthesist*, 44:345–50 (1995)). For example, it has been reported that these conditions developed in patients undergoing hemodialysis (Id.). It would therefore be desirable to develop new compositions and methods to deliver therapeutic amounts of GHB in vivo in a form that minimizes or eliminates the use of sodium ion.

In addition to problems associated with the delivery of the salt form of GHB, the half-life of GHB is relatively short (35 minutes, with peak plasma concentration occurring 20–60 minutes after oral administration), requiring more frequent administration of GHB to maintain its therapeutic effects. For example, it has been reported that increasing the dosing of GHB from three times a day to six times a day was beneficial in the treatment of alcoholism (Addolorato, et al., *The Lancet*, 351:38 (1998)), particularly for a patient population which did not respond well to less frequent dosages. Furthermore, in the treatment of narcoleptic patients, patients were found to benefit from two, or even three, doses of GHB during the night instead of a single dose which left patients wide awake before their planned awakening time (Scharf, *Sleep*, 21:507–14 (1998)). U.S. Pat. Nos. 4,599,355 and 4,738,985 to Kluger describe the use of ethyl 4-acetoxybutanoate to prolong sleep in a rat, increasing sleep duration with a large dose of this agent from about two hours with GHB to four hours. It therefore would be desirable to develop new compositions and methods to deliver therapeutic amounts of GHB in vivo that were longer acting, reducing the need for more frequent administration. Such formulations would have many advantages, including increased compliance, reduced medical care, and less intrusion, for example, allowing patients under treatment with narcolepsy and alcoholism to sleep uninterrupted.

It would also be desirable to develop new compositions and methods to deliver therapeutic amounts of GHB in vivo that provide a means to control delivery of GHB and plasma levels of GHB more precisely. Such compositions could be useful to raise effective dosages in vivo, as well as to prevent the development of hypernatremia and metabolic alkalosis at current dosage levels.

It is therefore an object of the present invention to provide compositions that deliver therapeutic amounts of GHB in vivo which minimize or eliminate undesirable side effects, for example, associated with co-delivery of sodium ions.

It is another object of the present invention to provide compositions for the deliver therapeutic amounts of GHB in vivo in formulations that are longer acting and reduce the need for frequent administration.

It is a further object to provide methods for delivering such compositions in vivo.

SUMMARY OF THE INVENTION

Oligomers and polymer compositions are provided which comprise GHB and produce GHB after administration in vivo. Devices for the storage and delivery of these polymers and oligomers are also provided. These oligomers and polymer compositions are useful in a variety of applications. The compositions can be used therapeutically, for example, in the treatment of patients with narcolepsy, chronic schizophrenia, catatonic schizophrenia, atypical psychoses, chronic brain syndrome, neurosis, alcoholism, drug addiction and withdrawal, Parkinson's disease and other neuropharmacological illnesses, hypertension, ischemia, circulatory collapse, radiation exposure, cancer, and myocardial infarction. Other uses for the compositions include anesthesia induction, sedation, growth hormone production, heightened sexual desire, anorectic effects, euphoria, smooth muscle relaxation, muscle mass production, and sleep, including rapid eye movement sleep. In a still further embodiment, the oligomers and polymers may be used to produce absence seizures.

DETAILED DESCRIPTION OF THE INVENTION

It was discovered that certain oligomers and polymers comprising GHB are suitable for delivering GHB in vivo. The oligomers and polymers are virtually or completely salt free, and can deliver GHB with a range of different and desirable pharmacokinetics. This includes prolonged release, steady state release, and controlled dosages, both low and high. These oligomers and polymers may be delivered in vivo by a variety of conventional methods, including oral and intravenous routes, as well as by implantation.

I. The GHB Compositions

The compositions include oligomers and/or polymers, which include GHB, and are provided in a pharmaceutically acceptable form for administration to patients.

Polymers and Oligomers

The oligomers and polymers include GHB, and may be produced by any number of methods including biological methods, such as fermentation, including transgenic fermentation systems, transgenic plant crops, chemical synthesis, and enzymatic synthesis. Preferred methods of preparation use fermentation, including transgenic fermentation, to produce the oligomers and polymers. These methods are described, for example, in Madison & Husiman, *Microbiol. & Mol. Biol. Rev.* 63:21–53 (1999); Williams & Peoples, *CHEMTECH*, 26:38–44 (1996); and Williams & Peoples, *Chem. Br.* 33:29–32 (1997). Molecular weights of polymers produced by these methods may be further tailored by subsequent chemical hydrolysis and/or transesterification. Combining fermentation production followed by hydrolysis or transesterification is a particularly preferred method for producing GHB containing oligomers with number average molecular weights (Mn) over 3,000, since chemical synthesis from gamma-butyrolactone is difficult (Lebedev & Yevstropov, *Makromol. Chem*. 185:1235–53 (1984)).

In preferred embodiments, the oligomers and polymers comprising GHB belong to a class of naturally occurring polyesters known as polyhydroxyalkanoates (PHAs). These materials are polyesters synthesized by numerous organisms in response to environmental stress. For reviews, see Byrom, "Miscellaneous Biomaterials," in Byrom, ed., *Biomaterials* MacMillan Publishers, London, 1991, pp. 333–59; Hocking & Marchessault, "Biopolyesters" in Griffin, ed., *Chemistry and Technology of Biodegradable Polymers*, Chapman and Hall, London, 1994, pp.48–96; Holmes, "Biologically Produced (R)-3-hydroxyalkanoate Polymers and Copolymers" in Bassett, ed., *Developments in Crystalline Polymers*, Elsevier, London, vol. 2, 1988, pp. 1–65; Lafferty et al., "Microbial Production of Poly-p-hydroxybutyric acid" in Rehm & Reed, eds., *Biotechnology*, Verlagsgesellschaft, Weinheim, vol. 66, 1988, pp. 135–76; Müller & Seebach, Angew. *Chem. Int. Ed. Engl*. 32:477–502 (1993); Steinbüchel, "Polyhydroxyalkanoic Acids" in Byrom, ed., *Biomaterials*, MacMillan Publishers, London, 1991, pp. 123–213; Williams & Peoples, *CHEMTECH*, 26:38–44, (1996), and the recent review by Madison & Husiman, *Microbiol. & Mol. Biol. Rev*. 63:21–53 (1999).

The preferred compositions may contain GHB alone, as in a homopolymer (or oligomer) of gamma-hydroxybutyrate, or may comprise GHB in a polymer or oligomer together with other monomers. For example, GHB be copolymerized with β-hydroxybutyrate, as in poly-β-hydroxybutyrate-co-γ-hydroxybutyrate, or copolymerized with two or more different monomers, including other hydroxyalkanoates or hydroxyacids. Examples of monomers which can be incorporated into GHB polymers and oligomers are identified in Williams, et. al., *Int. J. Biol. Macromol*., 25:111–21 (1999). A particularly preferred composition of the polymers and oligomers is poly-gamma-hydroxybutyrate (also known as poly-gamma-butyrolactone). Representative methods to prepare this polymer are described in PCT WO 99/32536 to Martin et al.; PCT WO 99/14313 to Huisman, et al., and references therein; Song et al., *Biotechnol. Lett*., 21:193–97 (1999); Saito et al., *Polymer International*, 39:169–74 (1996); and EP 0304293 to Doi. Polymers and oligomers comprising GHB also may be synthesized by methods described by Lebedev & Yevstropov, *Makromol. Chem*., 185:1235–53 (1984); Agostini, et al., *Polym. Sci*., Part A-1, 9:2775–87 (1971); Gross, et al., *Macromolecules*, 21:2657–68 (1988); Dubois, et al., *Macromolecules*, 26:4407–12 (1993); Le Borgne & Spassky, Polymer, 30:2312–19 (1989); Tanahashi & Doi, *Macromolecules*, 24:5732–33 (1991); Hori, et al., *Macromolecules*, 26:4388–90 (1993); Kemnitzer, et al., Macromolecules, 26:1221–29 (1993); Hori, et al., *Macromolecules*, 26:5533–34 (1993); Hocking & Marchessault, *Polym. Bull*., 30:163–70 (1993); and U.S. Pat. No. 5,563,239 to Hubbs, et al., and references therein. Chemo-enzymatic methods which can be used to prepare these polymers and oligomers are described in Xie et al., *Macromolecules*, 30:6997–98 (1997).

In addition to linear oligomers comprising GHB, cyclic oligomers comprising GHB may be especially useful for delivery of GHB in vivo. These may be prepared, for example, according to procedures described in Müller & Seebach, Angew. *Chem. Int. Ed. Engl*. 32:477–502 (1993).

In a further embodiment, polymers and oligomers may be prepared that do not contain GHB, but break down in vivo to GHB. An example of such a polymer is the bioerodible polyorthoester described in Sendelbeck & Girdis, *Drug Metabolism & Disposition*, 13:291–95 (1985).

Pharmaceutical Formulations

The polymers and oligomers comprising GHB can be made in several different physical forms, including latexes and dry powder. Methods to prepare suitable latexes are described in Horowitz, et al., *Macromolecules*, 32:3347–52 (1999) and PCT WO 99/35192 to Horowitz, et al., and references therein. Particulate, liquid, oil, viscous, and microdispersions forms are especially preferred for delivery. The polymers and oligomers may be used anywhere in the body of animals in a therapeutic amount to provide the desired effect. The polymers and oligomers can be prepared for enteral or parenteral administration by combining them with the appropriate delivery system. For enteral administration, they can be added, for example, to food, drink, or a dietary supplement. Other components may also be added to facilitate their delivery, such as flavoring, taste-masking, and coloring agents. The polymers and oligomers also may be formulated into tablets or encapsulated.

In one embodiment, the formulations of polymers and oligomers comprising GHB further comprise GHB monomer. The monomer of these formulations can provide an initial (spike) release of GHB, while the polymer or oligomer is being metabolized, thereby providing a delayed and/or sustained release.

For parenteral administration, the polymers and oligomers can be solubilized, if necessary, or suspended in a carrier for injection. The polymers and oligomers may, for example, be mixed or suspended in oils, solutions, saline, phosphate buffered solutions, and even very short oligomers of GHB. The monomer, GHB, or other active agents, may also be included in a formulation if desired.

Doses of the oligomers will vary with the desired therapy and will depend on the inclusion or exclusion of GHB monomer in the dose. Doses will generally provide effective concentrations of GHB in vivo equivalent to the oral administration of 10 to 100 mg/kg of the sodium salt of GHB. For example, oral doses of GHB oligomers can vary from about 10 mg/kg to more than 1 g/kg, with typical doses being 50 to 500 mg/kg. Release of GHB in vivo also may be controlled by preparing oligomers and polymer of different molecular weights, as well as by incorporating different monomeric units into the GHB containing oligomers and polymers.

Other Agents

The compositions can further include other therapeutic or prophylactic agents. Examples of such agents include compounds having anti-microbial activity, anesthetics, adjuvants, antiinflammatory compounds, stimulants, antidepressants, surfactants, steroids, lipids, enzymes, antibodies, and hormones.

II. Applications for the GHB Compositions

The oligomers and polymers may be administered in any case where it is considered desirable to elevate in vivo levels of GHB, particularly over an extended period of time (e.g., sustained release), such as several hours or days. They may be used for human medical and veterinary use. The oligomers and polymers may be used therapeutically in the treatment of patients with narcolepsy, chronic schizophrenia, catatonic schizophrenia, atypical psychoses, chronic brain syndrome, neurosis, alcoholism, drug addiction and withdrawal, Parkinson's disease, other neuropharmacological illnesses, and hypertension, fibromyalgia, and chronic fatigue syndrome. Other uses include administering the oligomers and polymers to provide GHB as an anti-angiogenic agent to treat cancer, and as prokinetic drugs to increase gastric emptying to treat malabsorption disorders and increase uptake of poorly absorbed drugs. The oligomers and polymers may also be used to induce anesthesia, sedation, growth hormone production, anorectic effects, euphoria, smooth muscle relaxation, muscle mass production, heightened sexual desire, sleep (including rapid eye movement sleep) and prolactin release. The oligomers and polymers may also be used to produce absence seizures, particularly in animal models. The oligomers and polymers may be used to treat or prevent inflammation and damage due to ischemia or reperfusion. The therapy may also be used in conjunction with other treatments.

Methods and Devices for Administration of the Compositions

A variety of devices may be used for storing and administering the polymers and oligomers, as well as formulations thereof. A preferred method of administration uses a syringe and needle. For certain treatments the polymers and oligomer formulations will be sold in a kit form, including the polymeric formulation in a reservoir in combination with delivery means such as a syringe or catheter, or solution to dissolve or resuspend the polymeric formulation. The polymers and oligomers may be placed in a delivery system to modulate or control the delivery of GHB. The formulations may be sterilized by filtration, irradiation, steam, or treatment with ethylene oxide, whichever is most suitable.

The present invention will be further understood with reference to the following non-limiting examples.

EXAMPLE 1

Preparation of Oligomers of GHB

Eight and a half (8.5) grams of PHA4400 (poly-4-hydoxybutyric acid, MW 430,000) was dissolved in 280 ml of anhydrous THF, to produce a 3% (wt./vol.) solution. Gentle heating to 60° C. was applied to facilitate dissolution of the polymer. One milliliter of absolute ethanol was slowly added to the solution, and the solution was cooled to room temperature. Aliquots of sodium methoxide (0.1 M in methanol) was added to provide desired molecular weight of product, as shown in Table I below. The solution was stirred at room temperature for 10 minutes, and the reaction quenched with acid. The resulting mixture was filtered and the THF evaporated to yield the product (7.5 g for 300 μL added sodium methoxide).

TABLE 1

Molecular Weight of GHB Oligomers

| Amount MeONa (μL) Added | GPC Ret. Time (min.) | Molecular Mass |
|---|---|---|
| 0 (starting material) | 7.87 | 430,000 |
| 100 | 8.0 | 320,000 |
| 200 | 8.6 | 82,000 |
| 300 | 9.1 | 25,000 |

Log MW = GPC Ret. Time*(−0.984) + 13.376, to determine relative to polystyrene

EXAMPLE 2

Digestibility of GHB Oligomers in Normal Rats

Thirty-nine male Sprague-dawley rats were acclimated to a controlled environment for one week. After fasting overnight, the rats weighed 244±21 g.

The rats were separated into three groups and treated as follows:

(i) 3 control rats were gavaged with 1.5 ml of TWEEN™ and were decapitated after 1 hour.

(ii) 12 rats were gavaged with 50 mg/kg of sodium GHB monomer (=0.4 mmol/kg) in 1.5 ml of TWEEN™ and decapitated in groups of three after 0.5, 1, 2, and 4 hours.

(iii) 24 rats were gavaged with 138 mg/kg of GHB oligomer (=1.6 mmol GHB equiv./kg, MW 25,000) in 1.5 ml TWEEN™) and decapitated in groups of three or four after 0.5, 1, 2, 4, 6, 8, and 10 hours.

Blood was collected at the time of decapitation and the serum was frozen for analysis. Serum samples (0.25 ml) were spiked with 200 nmol of $[^2H_6]$ 4HB. Serum samples were deproteinized with sulfosalicylic acid and centrifugation, and the acidic solution was extracted with ether (3 times). Pooled extracts were concentrated and hydrolyzed with NaOH (1 ml, 10 mM). After evaporation, the residue was converted to the trimethylsilyl derivative. Gas chromatography-mass spectrometry analysis was performed using an Hewlett-Packard MS-engine in the ammonia positive chemical ionization mode using an HP-5 column (47 m). Ions were monitored for unlabeled GHB at m/z 249 and m/z 255 for the $[^2H_6]$ GHB (internal standard), both as the trimethyl silyl derivatives.

A standard curve of GHB in dog plasma was generated using the isotope dilution of GC-MS assay described above. This curve was linear in the range of o to 100 nmol, with a detection limit of 1–2 nmol.

Results

As shown in Table 2, the baseline concentration of GHB in rat serum was found to be 9.12±1.47 μM in the rats gavaged with TWEEN™ only. After gavage with GHB monomer, the serum concentration of GHB increased transiently to 182±158 μM within 0.5 hour and rapidly decreased to baseline values within 2 hours. After gavage with GHB oligomer, the serum concentration of GHB increases to 86.5±21.8 μM within 0.5 hour and remained elevated at approximately 3 to 5 times the baseline value for over 10 hours.

TABLE 2

Concentration of GHB in the Serum of Rats Following Gavage with Tween (Control), Tween plus GHB, and Tween plus GHB Oligomer

| Time After Gavage (hr.) | GHB Monomer [GHB] (μM) | GHB Oligomer [GHB] (μM) |
|---|---|---|
| 1 (Control) | 9.12 ± 1.47 | 9.12 ± 1.47 |
| 0.5 | 182 ± 158 | 86.5 ± 21.8 |
| 1 | 23.2 ± 2.05 | 58.3 ± 19.5 |
| 2 | 12.8 ± 2.62 | 46.5 ± 13.4 |
| 4 | 14.9 ± 3.31 | 25.1 ± 2.48 |
| 6 | — | 60.1 ± 7.03 |
| 8 | — | 29.3 ± 14.5 |
| 10 | — | 35.4 ± 11.5 |

These results demonstrate that the GHB oligomer is digested in the rat and that it provides a sustained release of the monomer, over at least 10 hours. The amount of GHB in the serum was elevated between about 3 and about 8 times that of the baseline values over a period of 1 to 10 hours. These results are not explained by the mere presence of the monomer in the oligomer preparation, as the monomer is quickly (e.g., within 1–2 hours) absorbed and cleared from the circulation.

Those skilled in the art will recognize, or be able to ascertain using no more than routine experimentation, many equivalents to the specific embodiments of the invention described herein. The references cited herein are hereby incorporated by reference.

We claim:

1. A composition for modulating endogenous levels of gamma-hydroxybutyrate in a patient comprising a dosage formulations in a form acceptable for enteral or parenteral administration to a patient in need thereof, the formulation comprising a polymer or oligomer which comprises a gamma-hydroxybutyrate in an ester or polyester form, wherein the polymer or oligomer, When administered to the patient, is metabolized to release an effective amount of the gamma-hydroxybutyrate in vivo.

2. The composition of claim 1 wherein the polymer or oligomer is poly-gamma-hydroxybutyrate.

3. The composition of claim 1 wherein the polymer or oligomer is a copolymer comprising gamma-hydroxybutyrate.

4. The composition of claim 3 wherein the copolymer further comprises a second hydroxyalkanoate monomer.

5. The composition of claim 4 wherein the copolymer is poly-$\beta$-hydroxybutyrate-co-$\beta$-hydroxybutyrate.

6. The composition of claim 1 wherein the oligomer is a cyclic oligomer.

7. The composition of claim 1 further comprising gamma-hydroxybutyrate monomer.

8. The composition of claim 1 in a formulation suitable for intravenous administration.

9. The composition of claim 1 in a formulation suitable for oral administration.

10. The composition of claim 1 in a formulation suitable for implantation.

11. The composition of claim 1 wherein the polymers and oligomers are derived from biomass.

12. The composition of claim 1 in a dosage formulation for the treatment of patients having a disease selected from the group consisting of narcolepsy, chronic schizophrenia, catatonic schizophrenia, atypical psychoses, chronic brain syndrome, neurosis, alcoholism, drug addiction and withdrawal, Parkinson's disease and other neuropharmacological illnesses, hypertension, ischemia, circulatory collapse, radiation exposure, cancer, myocardial infarction, fibromyalgia, and chronic fatigue syndrome, reperfusion, and inflammation.

13. The composition of claim 1 in a dosage formulation to induce a condition selected from the group consisting of anesthesia, sedation, growth hormone production, anorectic effects, euphoria, smooth muscle relaxation, muscle mass production, heightened sexual desire, sleep, and prolactin release.

14. The composition of claim 1 in a dosage formulation suitable to produce absence seizures.

15. The composition of claim 1 that can elevate gamma-hydroxybutyrate levels in vivo for more than four hours.

16. A method of modulating gamma-hydroxybutyrate levels in vivo comprising administering to a human or animal a polymer or oligomer composition comprising gamma-hydroxybutyrate in an ester or polyester form wherein the composition is in a form acceptable for enteral or parental administration.

17. The method of claim 16 wherein the composition produces a gamma-hydroxybutyrate level effective to treat patients with a disorder selected from the group consisting of narcolepsy, chronic schizophrenia, catatonic schizophrenia, atypical psychoses, chronic brain syndrome, neurosis, alcoholism, drug addiction and withdrawal, Parkinson's disease and other neuropharmacological illnesses, hypertension, ischemia, circulatory collapse, radiation exposure, cancer, myocardial infarction, reperfusion, and inflammation.

18. The method of claim 17 wherein the patient has cancer and the composition provides for the sustained release of gamma-hydroxybutyrate in an anti-angiogenically effective amount.

19. The method of claim 16 wherein the composition produces a gamma-hydroxybutyrate level effective to induce a condition selected from the group consisting of anesthesia, sedation, growth hormone production, anorectic effects, euphoria, smooth muscle relaxation, muscle mass production, heightened sexual desire, and sleep.

20. The method of claim 16 wherein the composition is administered orally or by injection or implantation.

21. The method of claim 16 wherein the composition is administered as a hypnotic.

22. The method of claim 16 wherein the composition is administered as a neurotransmitter or neuromodulator.

23. The method of claim 16 wherein the composition is administered to increase gastric emptying or to treat malabsorption disorders.

24. A method for making oligomers comprising gamma-hydroxybutyrate comprising the steps:

a) selecting a polymer comprising gamma-hydroxybutyrate, and b) hydrolyzing or transesterifying the polymer to produce oligomers having number average molecular weights above 3,000.

25. A therapeutic composition comprising a gamma-hydroxybutyrate prodrug in an ester or polyester form in a polymer or oligomer that can modulate endogenous levels of gamma-hydroxybutyrate in vivo wherein the composition is in a form acceptable for enteral or parenteral administration.

26. The composition of claim 25 wherein the gamma-hydroxybutyrate prodrug is an orthoester.

27. The composition of claim 25 wherein the polymers and oligomers are derived from gamma-butyrolactone.

28. The composition of claim 25 wherein the polymers or oligomers are used for the slow or sustained release of gamma-hydroxybutyrate.

29. The method of claim 16 wherein the polymers or oligomers are used to treat cancer or prevent metastasis.

* * * * *